United States Patent
Carter et al.

(10) Patent No.: US 7,972,299 B2
(45) Date of Patent: Jul. 5, 2011

(54) BALLOON CATHETER WITH DEFLATION MECHANISM

(75) Inventors: Matthew P. Carter, Dobson, NC (US); Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 313 days.

(21) Appl. No.: 12/168,432

(22) Filed: Jul. 7, 2008

(65) Prior Publication Data
US 2009/0018500 A1 Jan. 15, 2009

Related U.S. Application Data

(60) Provisional application No. 60/958,819, filed on Jul. 9, 2007.

(51) Int. Cl.
*A61M 29/00* (2006.01)
(52) U.S. Cl. ............... 604/99.01; 604/96.01; 604/98.01; 604/103.09
(58) Field of Classification Search .... 604/96.01–97.01, 604/98.01, 99.01, 103, 103.09
See application file for complete search history.

(56) References Cited

U.S. PATENT DOCUMENTS

| 5,209,727 | A | * | 5/1993 | Radisch et al. ............ 604/96.01 |
| 5,423,755 | A | | 6/1995 | Kesten et al. |
| 5,454,788 | A | * | 10/1995 | Walker et al. .............. 604/99.04 |
| 6,033,381 | A | * | 3/2000 | Kontos ..................... 604/164.13 |
| 6,428,568 | B2 | * | 8/2002 | Gaudoin et al. ............. 623/1.11 |
| 7,524,302 | B2 | * | 4/2009 | Tower ........................ 604/96.01 |
| 2001/0001114 | A1 | | 5/2001 | Tsugita et al. |
| 2004/0236366 | A1 | | 11/2004 | Kennedy, II et al. |
| 2007/0276426 | A1 | | 11/2007 | Euteneuer |
| 2010/0217185 | A1 | * | 8/2010 | Terliuc et al. .............. 604/96.01 |

FOREIGN PATENT DOCUMENTS
WO WO 92/15360 9/1992
WO WO 2007/054364 A2 5/2007
* cited by examiner

*Primary Examiner* — Nicholas D Lucchesi
*Assistant Examiner* — Gerald Landry, II
(74) *Attorney, Agent, or Firm* — Brinks Hofer Gilson & Lione

(57) ABSTRACT

A balloon catheter including an inflatable balloon affixed to a catheter. The proximal end of the balloon is fixedly connected to the distal end of the catheter, and the distal end of the balloon is supported by stiffening member that extends distally from the distal end of the catheter and through the interior of the balloon. The distal end of the catheter comprises one or more apertures that are in fluid communication with an inflation lumen extending through the catheter. A deflation mechanism is disposed about the stiffening member and is configured to facilitate the flow of an inflation fluid through the interior volume of the balloon and towards the aperture.

15 Claims, 5 Drawing Sheets

Fig. 4

BALLOON CATHETER WITH DEFLATION MECHANISM

CROSS-REFERENCE TO RELATED APPLICATIONS

This application claims the benefit of U.S. Provisional Application Ser. No. 60/958,819, filed Jul. 9, 2007, entitled "Balloon Catheter with Deflation Mechanism", the entire contents of which are incorporated by reference.

TECHNICAL FIELD

This invention relates to medical devices, and more particularly to balloon catheters that can be placed within a body lumen and inflated to perform various medical procedures. The invention is especially relevant to balloon catheters with balloons formed of non-elastomeric films or materials, wherein the film that forms the balloon is folded and unfolded during deflation and inflation, respectively, of the balloon.

BACKGROUND OF THE INVENTION

Balloon catheters are used to perform various medical procedures wherein the balloon is positioned within a body lumen or canal and subsequently inflated. In some of these medical procedures, such as in an angioplasty procedure, the balloon is inflated so as to expand the interior volume of the body canal. In this type of procedure, the balloon is expanded to apply pressure to the interior surface of the body canal to thereby compress any tissue protruding into the canal and thereby enlarge the interior volume thereof. Once the tissue has been compressed, and the body canal widened, the balloon is deflated and removed.

In other types of medical procedures, such as photodynamic therapy (PDT), a balloon catheter is used to align and stabilize the catheter within the body lumen. For example, the balloon catheter may be inflated under low pressure within a body lumen such as the esophagus. A therapeutic fiber optic device is then inserted into the catheter in the vicinity of the balloon. The therapeutic fiber optic device is then used to emit light waves to treat the surrounding tissue. In this procedure, the balloon is used to both align the catheter in the center of the body lumen, and to prevent the catheter from moving during the PDT procedure. The balloon of a typical PDT balloon catheter is relatively large as compared to balloon catheters for use in angioplasty procedures.

An example of a conventional balloon catheter 10 is shown in FIGS. 1-3. As best seen in FIG. 1, the balloon catheter 10 comprises a balloon 12 that is affixed to a catheter 14. The balloon 12 is typically manufactured from a non-elastomeric material (e.g., a semi-rigid or non-compliant material), and includes a distal neck or end 16, a proximal neck or end 18 and a central portion 20. The proximal end 18 of the balloon 12 is secured and sealed to the distal end 22 of the catheter 14 by an adhesive, ultrasonic welding, or some other method. The distal end 16 of the balloon 12 is similarly secured and sealed to an end cap 24 by an adhesive, ultrasonic welding, or some other method. The end cap 24 is affixed to the distal end 26 of a stiffening wire 28, which projects distally from the distal end 22 of the catheter 14. The proximal end 30 of the stiffening wire 28 is secured to a hub 32, which in turn is attached to the proximal end 34 of the catheter 14. The stiffening wire 28 provides lateral and longitudinal support to the distal end 16 of the balloon 12, while also providing a cross-sectional profile that is smaller than that of the catheter 14. This allows the balloon 12 to be folded or collapsed into a smaller profile for passage into and out of the patient.

The hub 32 is configured to be attached to a device, such as a syringe (not shown), that may be manipulated to either inflate or deflate the balloon 12 by injecting a fluid into or withdrawing a fluid from, respectively, the interior volume of the balloon 12. For example, the balloon 12 is inflated by injecting a fluid such as saline through the hub 32 and into the inflation lumen 38 of the catheter 14. The fluid passes through the inflation lumen 38 and into the interior volume of the balloon 12 via one or more apertures 36 in the distal end 22 of the catheter 14. Likewise, the balloon 12 is deflated by withdrawing the fluid from the interior volume of the balloon 12 via the apertures 36 and the inflation lumen 38 of the catheter 14.

Conventional balloon catheters for use in the above-described procedures, including those for use in PDT procedures, have several drawbacks. One such drawback is that conventional balloon catheters often require an inordinate amount of time to be deflated, which must be completely deflated before the balloon can be withdrawn from the patient. This can unnecessarily increase the duration of the procedure, with obvious negative consequences to the patient. Another drawback of conventional balloon catheters is that sometimes the balloon will not deflate completely. When this occurs, it may be difficult or impossible to withdraw the balloon from the patient, particularly when the balloon catheter has been introduced into the patient through an endoscope or other introducer device. Moreover, since it is often difficult to determine if and when a balloon has been completely deflated, the physician or assistant will sometimes attempt to withdraw the balloon from the patient prematurely. If this occurs, then the balloon may become lodged in the endoscope, or may tear and separate into pieces as it is being pulled into the distal end of the endoscope. Balloon catheters for use in PDT procedures, which have relatively large volume balloons, are particularly susceptible to the above-described problems.

FIGS. 2-3 illustrate the conventional balloon catheter 10 of FIG. 1 that will not deflate completely. In particular, and as shown in FIG. 2, as the balloon 12 begins to deflate, the interior surface of the balloon 12 as been drawn inwardly and into contact with the exterior surface of the stiffening wire 28. As further suction is applied to the balloon 12 (via inflation lumen 38), the proximal portion of the balloon 12 completely collapses about the stiffening wire 28, as illustrated in FIG. 3. Once the interior surface of the balloon 12 seals about the stiffening wire 28, any inflation fluid remaining within the distal portion of the balloon 12 becomes trapped within the balloon 12. Any further application of suction merely increases the seal between the interior surface of the balloon 12 and the stiffening wire 28, and will not result in egress of the fluid remaining in the balloon 12.

What is needed is an improved balloon catheter that overcomes the disadvantages of the conventional devices. In particular, what is needed is a balloon catheter that can be quickly and completely deflated to a minimal diameter for ingress and egress through the body's canals and/or an endoscope channel.

SUMMARY OF THE INVENTION

The foregoing problems are solved and a technical advance is achieved by the balloon catheter of the present invention. The balloon catheter includes a rounded or cylindrically shaped balloon that is affixed to a catheter. The balloon includes a distal end, a proximal end and a central portion, and may be formed of a non-elastomeric material. The proximal end of the balloon is fixedly attached to the distal end of the catheter, and the distal end of the balloon is fixedly attached to an end cap. The end cap is attached to the distal end of a stiffening wire, which projects distally from the distal end of the catheter and traverse the interior of the balloon. In one aspect of the invention, the end cap is fixedly attached to the stiffening wire. In another aspect of the invention, the end cap is slidably attached to the stiffening wire by a slip joint connection.

The catheter includes an inflation lumen extending therethrough. The proximal end of the catheter includes a hub that is configured to be attached to a source of inflation fluid such that inflation fluid can be injected into or withdrawn from the inflation lumen. The distal end of the catheter comprises one or more apertures in fluid communication with the inflation lumen and through which the inflation fluid can pass into or out from the interior of the balloon.

A deflation mechanism is disposed within the interior of the balloon and is configured to facilitate the passage of inflation fluid towards the apertures in the distal end of the catheter during deflation of the balloon. In one aspect of the invention, the deflation mechanism comprises a tubular member that is disposed over a portion of the stiffening wire that traverses the interior of the balloon. The tubular member has a circular cross-section, and has an inside diameter that is sufficiently large, relative to the outside diameter of the stiffening wire, to permit the flow of inflation fluid through and along the interior of the tubular member. The tubular member also comprises a plurality of openings disposed circumferentially and longitudinally therealong. The openings provide a means for egress of any inflation fluid trapped within a portion of the balloon during deflation. More specifically, any fluid trapped within a portion of the balloon will pass through the openings and into the interior of the tubular member, whereby the fluid can be directed towards the apertures in the distal end of the catheter, even if a portion of the balloon has collapsed and sealed against a portion of the stiffening wire and/or the tubular member.

In another aspect of the invention, the deflation mechanism comprises a tubular member disposed over the portion of the stiffening wire traversing the interior of the balloon, wherein the tubular member comprises a star-shaped cross-section defined by a plurality of peaks and valleys. The valleys are configured to permit the flow of inflation fluid therealong, and the peaks are configured to prevent the valleys from being occluded by the deflated balloon. More specifically, the valleys provide a means for egress of any inflation fluid trapped within a portion of the balloon during deflation, even if a portion of the balloon has collapsed and sealed against a portion of the stiffening wire and/or the tubular member. The tubular member may be integrally formed with the stiffening wire.

These and other advantages, as well as the invention itself, will become apparent in the details of construction and operation as more fully described below. Moreover, it should be appreciated that several aspects of the invention can be used with other types of balloon catheters or medical devices.

BRIEF DESCRIPTION OF THE DRAWING

Embodiments of the present invention will now be described by way of example with reference to the accompanying drawings, in which:

FIG. 4 depicts a cross-sectional side view of an illustrative embodiment of a balloon catheter in accordance with the teachings of the present invention;

DETAILED DESCRIPTION

Figure 1:
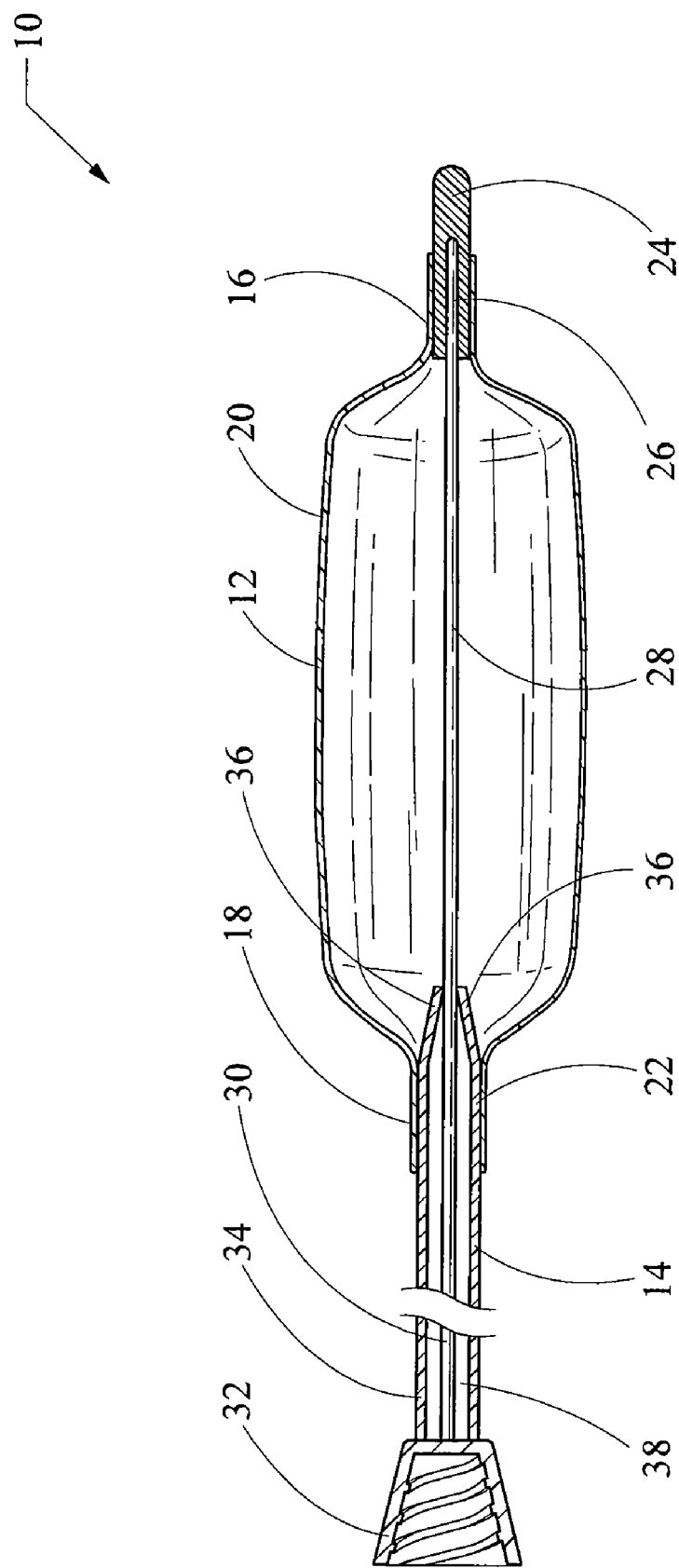
FIG. 1 depicts cross-sectional side view of a conventional balloon catheter in the inflated state.
Figure 2:
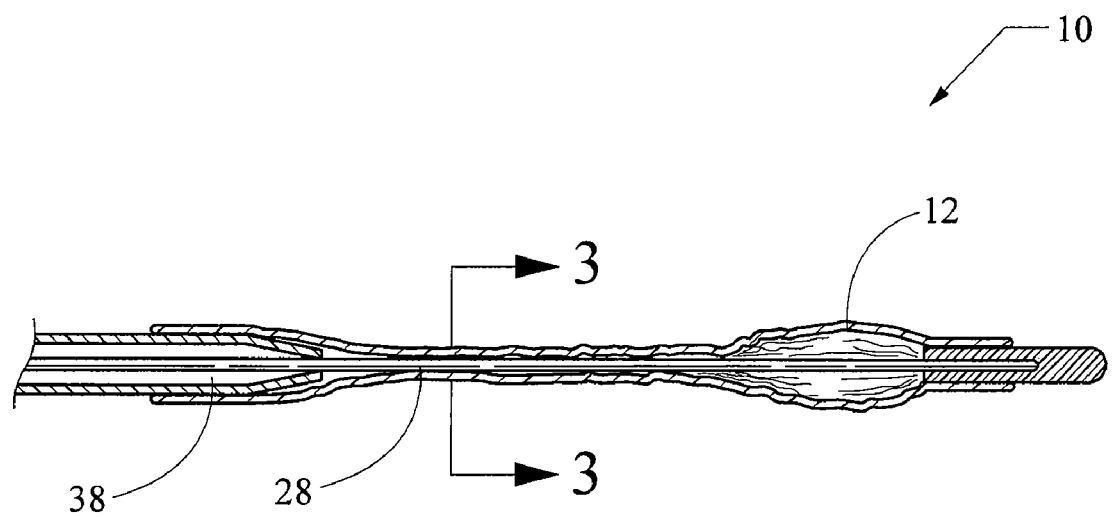
FIG. 2 depicts a cross-sectional side view of the distal portion of the balloon catheter of FIG. 1 in a partially deflated state.
Figure 3:
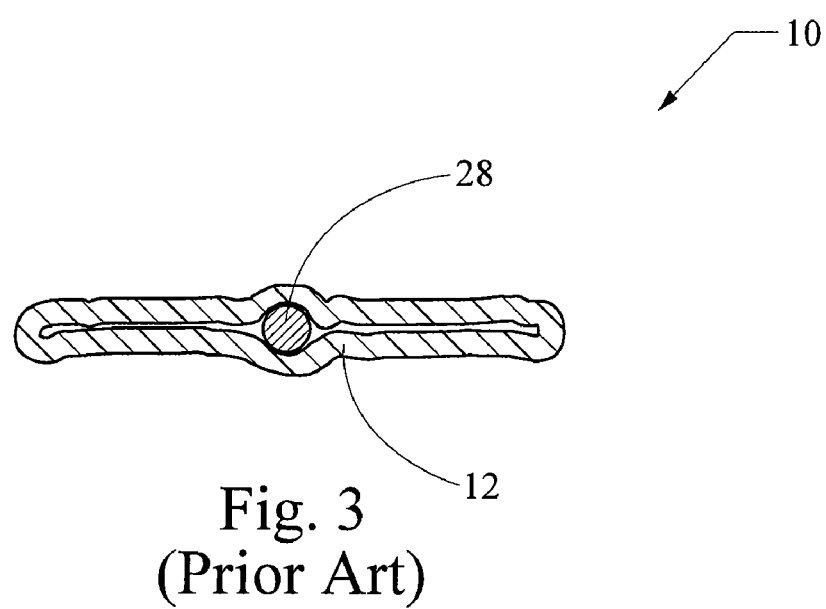
FIG. 3 is sectional view taken along line 3-3 of FIG. 2.
Figure 4:
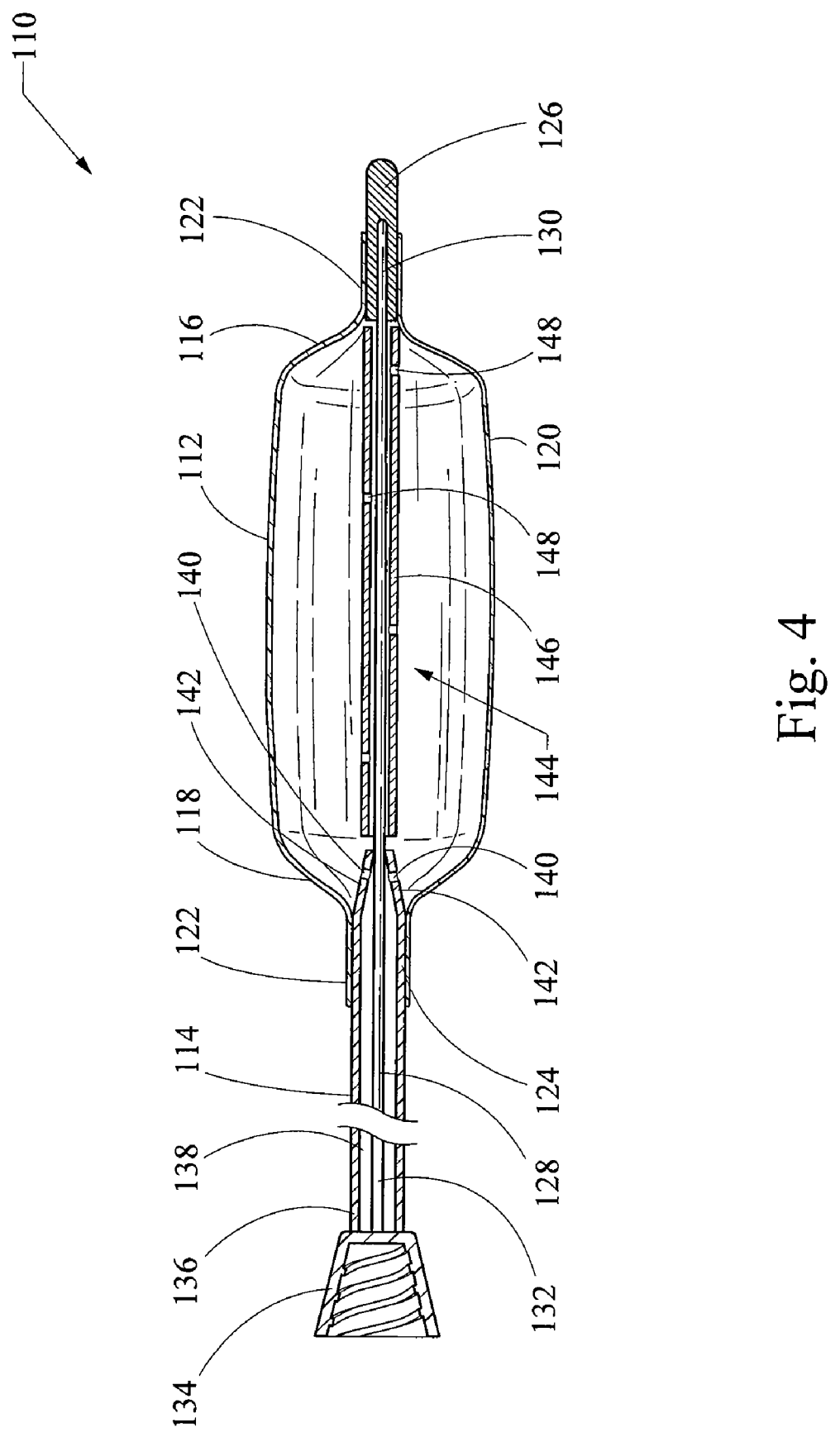

A first embodiment of a balloon catheter 110 of the present invention is illustrated in FIG. 4. The balloon catheter 110 includes a rounded, oval, cylindrical, bullet or other appropriately shaped balloon 112 that is affixed to a catheter 114. The balloon 112 is typically manufactured from a non-elastomeric material (e.g., a semi-rigid or non-compliant material), and preferably comprises a translucent, transparent or optically clear film. For example, the balloon 112 could be manufactured from a biocompatible polymer such as polyamide, polyurethane, polyester, polyolefin, polyethylene terephthalate and the like.

The balloon 112, as shown in the drawings, includes a conically shaped distal portion 116, a conically shaped proximal portion 118 and a cylindrically shaped central portion 120. However, different configurations or designs can also be utilized for the balloon 112. For example, the distal and proximal portions 116, 118 could comprise a curvilinear shape. The proximal and distal ends of the balloon 112 further comprise cylindrical neck portions 122, which provide a mechanism for securing and sealing the balloon 112 to other components of the balloon catheter 110 (i.e., to catheter 114 and end cap 126).

The central portion 120 of the balloon 112 may be provided with longitudinally or axially extending pleats or folds (not shown). These folds provide creases along which the surface of the balloon 112 will fold or pleat when deflated. The folds permit the central portion 120 of the balloon 112 to be collapsed to a minimal cross-sectional area or diameter, and prevent the formation of transverse or lateral creases along the same area.

The proximal end of the balloon 112 is attached to the catheter 114 by inserting the distal end 124 of the catheter 114 into the neck portion 122 attached to the proximal end of the balloon 112. The neck portion 122 is then affixed to the outer wall of the catheter 114 by an adhesive, ultrasonic welding, or some other method so as to anchor and seal the proximal end of the balloon 112 thereto. In the preferred embodiment shown, the inside diameter of the neck portion 122 is sized to fit tightly or snugly over the catheter 114 so as to improve the integrity of the seal between these two components.

The distal end of the balloon 112 is attached to an end cap 126, which encloses and seals the distal end of the balloon 112. The distal end of the balloon 112 is attached to an end cap 126 by inserting the proximal end of the end cap 126 into the neck portion 122 attached to the proximal end of the balloon 112. The neck portion 122 is then affixed to the outer wall of the end cap 126 by an adhesive, ultrasonic welding, or some other method so as to anchor and seal the distal end of the balloon 112 thereto. In the preferred embodiment shown, the inside diameter of the neck portion 122 is sized to fit tightly or snugly over the end cap 126 so as to improve the integrity of the seal between these two components. The distal end of the end cap 126 is preferably rounded to facilitate advancement of the balloon catheter 110 through the bodily lumens of the patient. Likewise, the distal end of the end cap 126 may also be tapered and/or made from a flexible material.

A stiffening wire (mandrel) 128 projects distally from the distal end 124 of the catheter 114 and traverses the interior of the balloon 112. The distal end 130 of the stiffening wire 128 is fixedly connected to the end cap 126, and provides longitudinal and lateral support to the distal end of the balloon 112. The diameter of the stiffening wire 128 is smaller than that of the catheter 114, thereby allowing the balloon 112 to be folded into a smaller cross-sectional area than would be possible if the catheter 114 extended through the interior of the balloon 112. Preferably, the cross-section area of the collapsed and folded balloon 112 is not substantially larger than the cross-sectional area of the catheter 114. The stiffening wire 128 extends proximally through the catheter 114 and is attached at its proximal end 132 to a hub 134, which in turn is connected to the proximal end 136 of the catheter 114. In the particular embodiment illustrated, the stiffening wire 128 passes through the inflation lumen 138 of the catheter 114. Alternatively, the stiffening wire 128 may be disposed in a separate lumen of the catheter 114. The catheter 114 may also comprise additional lumens through which contrast fluids or guide wires (not shown) can be passed.

The hub 134 is configured for attachment to an inflation device, such as a standard medical syringe (not shown), for providing an inflation fluid to inflate the balloon 112. More specifically, an inflation fluid, such as saline, is injected though the hub 134 and into the lumen 138. The inflation fluid then passes through the lumen 138 and into the interior of the balloon 112 via one or more apertures 140 provided in the distal end 124 of the catheter 114. The balloon 112 is deflated by withdrawing the inflation fluid from the interior of the balloon 112 via the apertures 140, lumen 138 and hub 134. In the particular embodiment illustrated, the apertures 140 are disposed in a tapered insert 142 that is press fit into or otherwise secured to the distal end 124 of the catheter 114. The tapered shape of the insert 142 is configured to prevent the apertures 140 from being occluded by the balloon 112 as it is being deflated.

A deflation mechanism 144 is disposed about the portion of the stiffening wire 128 that traverses the interior of the balloon 112. As will be explained in detail below, the deflation mechanism 144 is configured to facilitate the passage of inflation fluid towards the apertures 140 at the distal end 124 of the catheter 114 during deflation of the balloon 112. In the embodiment illustrated, the deflation mechanism 144 comprises a tubular member 146 having a circular or cylindrical cross-section with a central passageway 147 longitudinally extending therethrough. The inside diameter of the tubular member 146 (i.e., the diameter of passageway 147) is sufficiently large, relative to the outside diameter of the stiffening wire 128, to permit the flow of inflation fluid through and along the interior of the tubular member 146 (i.e., through passageway 147). However, the outside diameter of the tubular member 146 is preferably smaller than the outside diameter of the catheter 114, thereby providing space for the collapsed and folded balloon 112 thereabout. In the particular embodiment illustrated, the tubular member 146 has an outside diameter of about 0.58 inches and an inside diameter of about 0.45 inches. The outside diameter of the stiffening wire 128 is about 0.26-0.27 inches. Thus, there is a circumferential gap of about 0.09 inches between the inside of the tubular member 146 and the outside of the stiffening wire 128. Alternatively, the inside diameter of the tubular member 146 could be provided with grooves or flow channels through which the inflation fluid will flow, thereby minimizing or eliminating the need for a gap between the inside of the tubular member 146 and the outside of the stiffening wire 128. Such an arrangement may allow the use of a smaller diameter tubular member 146.

Figure 5:
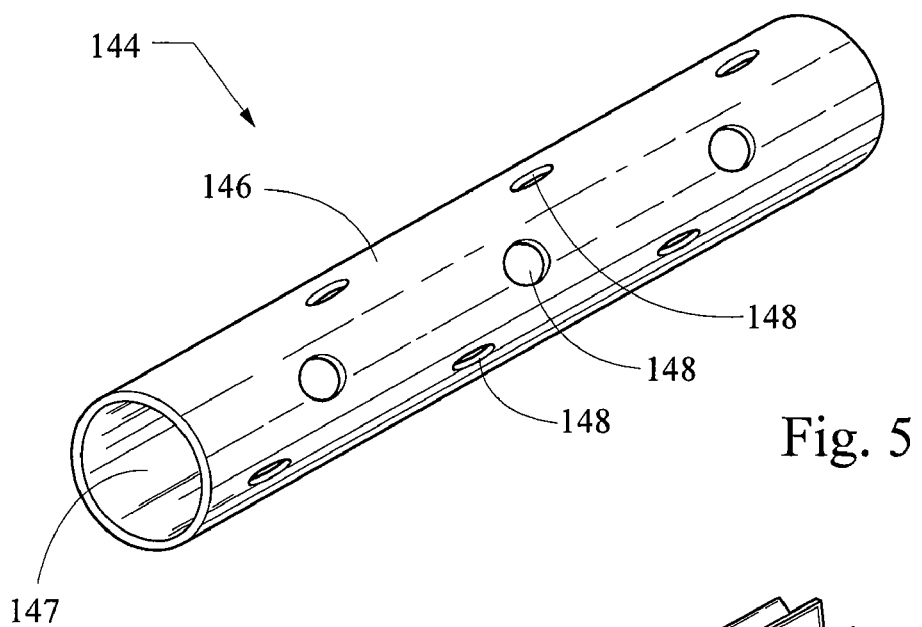
FIG. 5 is a perspective view of the deflation mechanism utilized in the balloon catheter of FIG. 4.

The tubular member 146 also comprises a plurality of openings 148 disposed circumferentially and longitudinally therealong. The openings 148 provide a means for egress of any inflation fluid trapped within a portion of the balloon 112 during deflation. More specifically, any fluid trapped within a portion of the balloon 112 will pass through the openings 148 and into the interior of the tubular member 146, whereby the fluid can be directed (flow) towards the apertures 140 in the distal end 124 of the catheter 114, even if a portion of the balloon 112 has collapsed and sealed against a portion of the stiffening wire 128 and/or the tubular member 146. As best seen in FIG. 5, which is a perspective view of tubular member 146, the openings 148 are disposed circumferentially about the tubular member 146 in a spiral pattern. However, other patterns or arrangements for the openings 148 can be utilized so long as the distance between any portion of the balloon 112 and at least one opening 148 is kept to a minimum.

In the particular embodiment illustrated in FIG. 4, tubular member 146 has a length that is slightly shorter than the length of the portion of the stiffening wire 128 that traverses the interior of the balloon 112. In other words, the tubular member 146 has a length that is less than the distance between the distal face of the insert 142 and the proximal face of the end cap 126. This allows the tubular member 146 to "float" on the stiffening wire 128, which prevents the tubular member from interfering with the stiffening/centering function of the stiffening wire 128, or the shape of the balloon 112 as it is inflated or deflated. This also allows any inflation fluid passing through the interior of the tubular member 146 to freely pass into or out of the ends of the tubular member 146. In the particular embodiment illustrated, the length of the tubular member is 1-2 mm less than the distance between the distal face of the insert 142 and the proximal face of the end cap 126. Alternatively or additionally, the ends of tubular member 146 may be scalloped to facilitate passage of inflation fluid at the ends thereof.

The tubular member 146 is preferably made from relatively rigid material so that it will not collapse or accordion as the balloon 112 is being deflated. In the embodiment illustrated, the tubular member is manufactured from polyetheretherketone (PEEK), but other materials having suitable properties can also be utilized.

Figure 6:
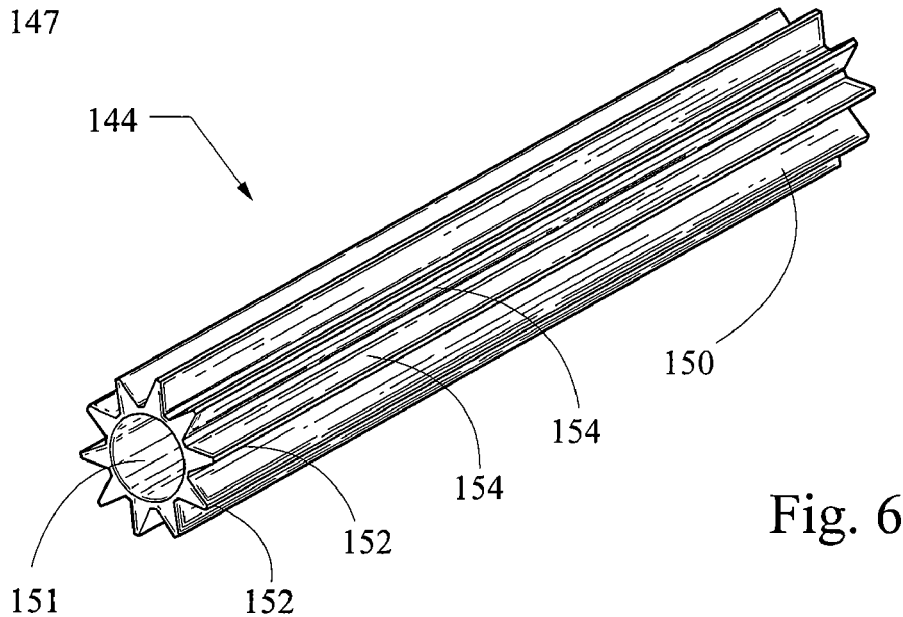
FIG. 6 is a perspective view of an alternative embodiment of a deflation mechanism that may be utilized in the balloon catheter of FIG. 4.
Figure 7:
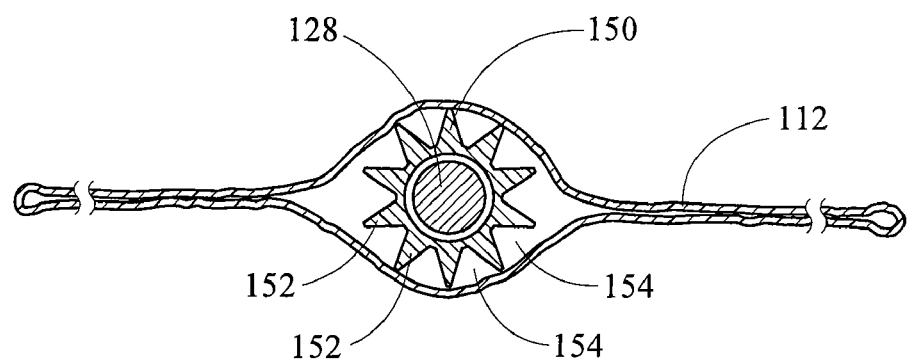
FIG. 7 is a cross-sectional view of the deflation mechanism of FIG. 6 disposed within a partially deflated balloon.

FIGS. 6-7 illustrate an alternative embodiment of the deflation mechanism 144. As best seen in FIG. 6, the deflation mechanism 144 comprises a tubular member 150 having a star-shaped cross-section defined by a plurality of peaks 152 and valleys 154 alternately disposed about the circumference thereof. The valleys 154 are configured to permit the flow of inflation fluid therealong, and the peaks 152 are configured to prevent the valleys 154 from being occluded by the deflated balloon 112. This is illustrated in FIG. 7, which is a cross-sectional view of a balloon 112 deflated about the tubular member 150. Thus, the valleys 154 provide a means for egress of any inflation fluid trapped within a portion of the balloon 112 during deflation, even if a portion of the balloon 112 has collapsed and sealed against a portion of the stiffening wire 128 and/or the tubular member 150.

Like the embodiment of FIGS. 4-5, the tubular member 150 is disposed over the portion of the stiffening wire 128 traversing the interior of the balloon 112. However, since the flow of inflation fluid is along the exterior surface of tubular member 150 (as opposed to the interior of tubular member 146), the inside diameter of tubular member 150 (i.e., the diameter of passageway 151) need not be significantly larger than out side diameter of the stiffening wire 128, although it should still be large enough that it will not interfere with the function or movement of the stiffening wire 128. Alternatively, the tubular member 150 may be integrally formed with the stiffening wire 128, thereby eliminating the need for separate components. In particular, the outside surface of the stiffening wire 128 could be provided with a plurality of peaks 152 and valleys 154 alternately disposed about the circumference thereof.

Other surfaces features could also be employed along the surface of tubular member 150 or stiffening wire 128 to provide a deflation mechanism 144 for directing the flow of inflation fluid through a partially or fully deflated balloon 112. For example, a series of bumps (not shown) could be disposed on the surface of the tubular member 150 (or stiffening wire 128), the bumps being configured to prevent the partially or fully deflated balloon 112 from sealing about the tubular member 150 (or stiffening wire 128). Spiral grooves are another example of a surface feature that could be employed to prevent the partially or fully deflated balloon 112 from sealing about the tubular member 150 (or stiffening wire 128).

Figure 8:
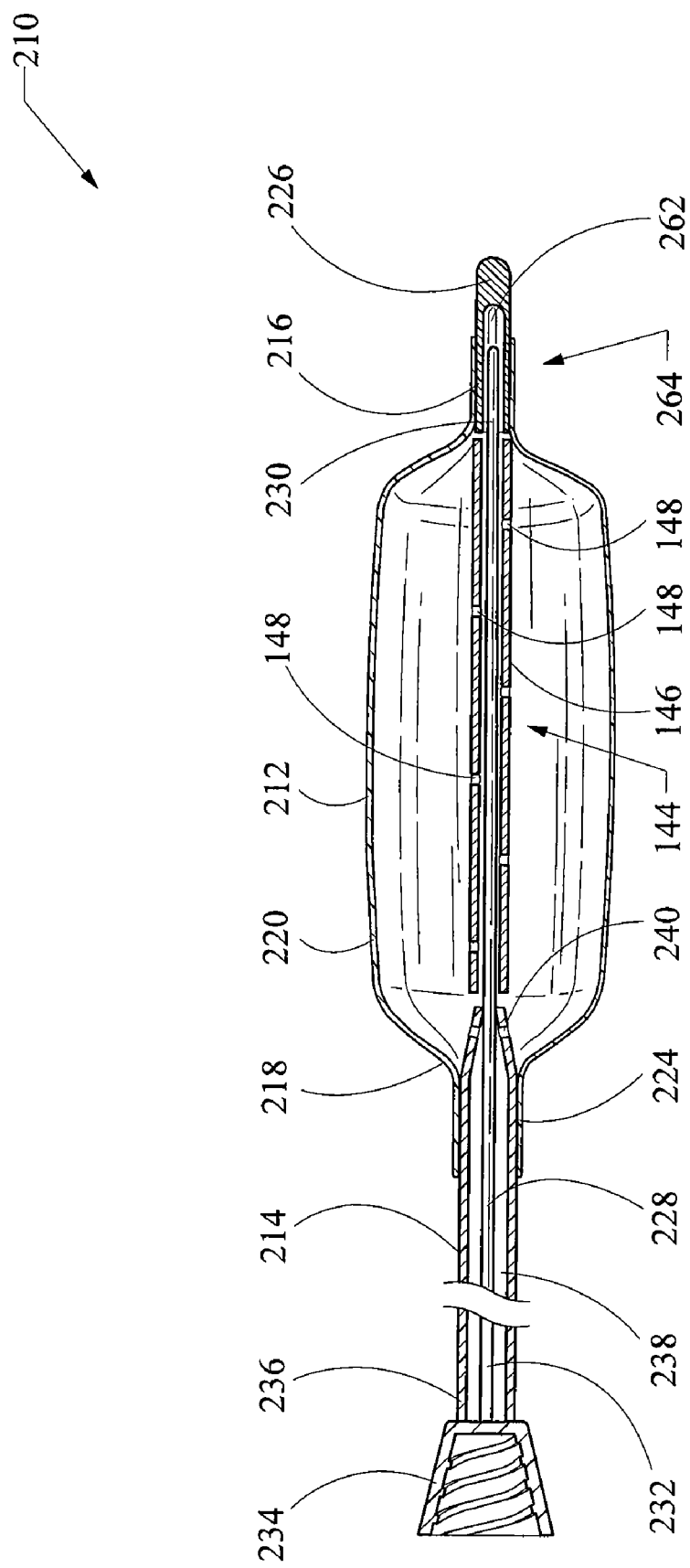
FIG. 8 is a cross-sectional side view of a second embodiment of a balloon catheter in accordance with the teachings of the present invention.

A second embodiment of a balloon catheter 210 of the present invention is depicted in FIG. 8. As will be described in greater detail below, the balloon catheter 210 of this embodiment comprises a slip joint connection 264 between the stiffening member 228 and the balloon 212, which prevents creasing of the balloon 212 and/or bending of the stiffening member 228 during inflation or deflation. Other aspects of the balloon catheter 210 are similar to the balloon catheter 110 of FIGS. 4-5. For example, the balloon catheter 210 comprises a flexible elongate outer catheter 214 that is fixedly connected at its distal end 224 to the proximal end 218 of the balloon 212. The proximal end 236 of outer catheter 214 includes a hub 234 comprising a luer fitting that is configured to attach to an inflation device such a standard medical syringe. The outer catheter 214 has a construction similar to that described in connection with the above described embodiment of FIG. 4.

The balloon catheter 210 further comprises an elongate stiffening member 228 disposed within the lumen 238 of the outer catheter 214. The diameter or cross-sectional area of the stiffening member 228 is generally less than the diameter or cross-sectional area of the lumen 238 so as to allow the passage of fluid between the hub 234 (i.e., the inflation device) and the interior of the balloon 212. In other words, the diameter of the stiffening member 228 is less than that of the lumen 238 so as to create a cavity between the outside surface of the stiffening member 228 and the inside surface of the lumen 238 sufficient for the passage of an inflation lumen. Alternatively, the outer catheter 214 may comprise a separate lumen for the passage of an inflation fluid.

As illustrated in FIG. 8, the stiffening member 228 is connected at or near its proximal end 232 to the hub 234. The distal end 230 of the stiffening member 228 extends distally from the distal end 224 of the outer catheter 214, through the interior of the balloon 212, and into a sleeve 262 formed in the distal end 216 of the balloon 212. In the embodiment shown, the sleeve 262 is formed by an end cap 226 fixed to the distal end 216 of the balloon 212. The end cap 226 provides an air tight seal with the balloon 212 and is rounded at its distal end to facilitate ingress of the balloon catheter 210 into and through the patient's bodily lumen and prevent the end cap 226 from puncturing or injuring the walls of the bodily lumen. The end cap 226 may be manufactured from a pliable plastic material to further promote the ingress of the balloon catheter 210 and reduce irritation that may be caused thereby.

The distal end 230 of the stiffening member 228 slidably engages with sleeve 262 to form a slip joint connection 264. This is in contrast with the embodiment of FIG. 4, wherein the distal end 130 of the stiffening member 128 is fixedly connected to the end cap 126 and thus, the distal end of the balloon 112. The slip joint 264 allows the distal end 216 of the balloon 212 to axially move or translate with respect to the distal end 230 of stiffening member 228. This configuration allows the overall axial or longitudinal length of balloon 212 to change during inflation or deflation without transferring tensile or compressive forces to either outer catheter 214 or stiffening member 228. For example, when the balloon 212 is deflated, the balloon 212 tends to elongate in the axial direction as the central portion 220 is drawn inwardly towards the catheter 214, thereby moving the distal end 216 of the balloon 212 distally from or relative to the distal end 224 of the catheter 214. Since the distal end 216 of the balloon 212 is not prevented from moving axially, transverse creasing of the central portion 220 of the balloon 212 during deflation is eliminated or at least minimized. Moreover, the central portion 220 of the balloon 212 can be collapsed into a smaller diameter or cross-section for ingress or egress of the balloon catheter 210 through the body's canals and/or the endoscope channel.

The slip joint 264 also prevents the application of adverse forces on the catheter 214 by the balloon 212 during inflation or deflation of the device. In particular, since the distal end 216 of the balloon 212 is not connected to the distal end 224 of the catheter 214, any axial contraction or expansion of the balloon 212 will not impart any tensile or compressive forces onto the catheter 214. In other words, the catheter 214 will not be bowed or stretched as result of the inflation or deflation of the balloon 212. Consequently, the catheter 214 should remain centered with respect to cross-sectional area of the balloon 212 irrespective of the state of inflation of the balloon 212.

The advantages provided by the slip joint 264 are particularly advantageous for PDT balloons, which require that the catheter 214 be accurately centered within the bodily lumen of the patient. Other aspects of the balloon catheter 210, and in particular the configuration and arrangement of the slip joint 264, stiffening member 228, and end cap 226, are disclosed in U.S. Provisional Application No. 60/922,769, filed Apr. 10, 2007, and entitled "Non-Buckling Balloon Catheter With Spring Loaded Floating Flexible Tip", the entire contents of which are incorporated herein by reference. For example, this provisional application discloses a nitinol stiffening member having a tapered distal end that is disposed within a coil spring, and which is slidably engaged with an elongated polyurethane end cap. As explained therein, the arrangement provides a particularly flexible catheter tip that is nevertheless kink resistant. Other aspects of slip-jointed balloon catheters are disclosed in US 2003/0236495 and US 2004/0236366, both entitled "Non-Buckling Balloon Catheter", the entire contents of which are incorporated herein by reference.

Similar to the embodiment of FIG. 4, the balloon catheter 210 illustrated in FIG. 8 includes a deflation mechanism 144 comprising a tubular member 149 having a plurality of openings 148 disposed therealong. The deflation mechanism 144 is likewise configured to facilitate the passage of inflation fluid towards the apertures 240 at the distal end 224 of the catheter 214 during deflation of the balloon 212. Other aspects of the deflation mechanism 144, and in particular tubular member 146, are the same as described above in connection with FIGS. 4-5 and will therefore not be repeated here.

Tubular member 146 may provide an additional function for the balloon catheter 210 of FIG. 8. As explained above, the slip joint connection 264 allows the distal end 216 of the balloon 212 to axially move or translate relative to the distal end 230 of the stiffening member 228. This allows the balloon 212 to collapse and fold during deflation unrestrained by the stiffening member 228. However, the unconstrained balloon 212 tends to fold into a 2-wing configuration during deflation, which has a larger cross-sectional area than if folded into a 3-wing or 4-wing configuration (as illustrated in FIG. 7). This larger cross-sectional area may inhibit removal of the balloon catheter 210 from the patient. Moreover, it is possible that the central portion 220 of the balloon 212 may accordion, or that the distal end 216 of the balloon 212 may invert, during deflation of the balloon 212, particularly if the balloon 212 is deflated rapidly or if the user attempts to pull the balloon 212 into the introducer before it has been completely deflated. Tubular member 146 may be sized to promote higher wing folding configurations, and/or prevent these other problems from occurring during deflation. In particular, the tubular member 146 may be configured to act as back stop or spacer to prevent the distal end 216 of the balloon 212 from moving too far proximally during deflation. This is accomplished by providing a tubular member 146 having a length that is approximately equal to the shortest desired spacing between the distal end 224 of the catheter 214 and the proximal face of the end cap 226. However, the tubular member 146 should still be configured so as to not interfere with the functional movement of the slip joint 264 and its intended operation.

Although the embodiments described above generally include a catheter affixed to the proximal end of the balloon, and a separate stiffening member that supports (either fixedly or slidably) the distal end of the balloon, it should be understood that other catheter types and arrangements can be employed. For example, the stiffening member may not extend to the proximal end of the catheter, or may be eliminated altogether. Such designs and arrangements are well known to those skilled in the art.

Likewise, although the embodiments described above generally include a balloon manufactured from a non-elastomeric material (e.g., a semi-rigid or non-compliant material). However, it should be understood that a balloon manufactured from an elastomeric or complaint material can be also be employed. Balloons of this type are typically employed in balloon catheters that are used for extraction or occlusion procedures. In any event, it should be understood that the deflation mechanism of the present invention can be utilized in these types of compliant balloon catheters, and can provide the same advantages described above in connection with non-compliant balloon catheters.

Any other undisclosed or incidental details of the construction or composition of the various elements of the disclosed embodiments of the present invention are not considered to be critical to the achievement of the advantages of the present invention, so long as the elements possess the attributes required to perform as disclosed herein. The selection of these and other details of construction are believed to be well within the ability of one of ordinary skill in the relevant art in view of the present disclosure. Illustrative embodiments of the present invention have been described in considerable detail for the purpose of disclosing practical, operative structures whereby the invention may be practiced advantageously. The designs described herein are intended to be exemplary only. The novel characteristics of the invention may be incorporated in other structural forms without departing from the spirit and scope of the invention.

What is claimed is:

1. A balloon catheter comprising:
   a inflatable balloon comprising a balloon wall defining an interior volume, the balloon further comprising a distal end, a proximal end, and a central portion disposed therebetween;
   a catheter comprising an elongated shaft extending along an axis between a distal end portion and a proximal end portion, the proximal end portion comprising a connector configured to engage an inflation device, the distal end portion fixedly connected to the proximal end of the balloon, the distal end portion comprising an aperture near the proximal end of the balloon, a lumen extending through the shaft and in fluid communication with the interior volume of the balloon via the aperture;
   a stiffening member extending distally from the distal end portion of the catheter and through the interior volume of the balloon, the stiffening member being engaged with the distal end of the balloon; and
   a deflation mechanism disposed at least partially about the stiffening member, the deflation mechanism configured to facilitate the flow of an inflation fluid through the interior volume of the balloon and towards the aperture,
   wherein an end cap is fixedly connected to the distal end of the balloon and the stiffening member is engaged with the end cap, the end cap comprising a sleeve extending partially therethrough, the sleeve being defined by an interior volume of the end cap, and further wherein the stiffening member is slidably engaged with the sleeve of the end cap such that axial movement of the distal end of the balloon relative to the proximal end of the balloon in a direction generally parallel to the axis of the shaft is not restrained by the stiffening member, and
   wherein the distal end of the stiffening member comprises a tapered portion that is disposed within a coil spring.

2. The balloon catheter according to claim 1 wherein the deflation mechanism comprises a tubular member disposed within the interior volume of the balloon and between the distal end portion of the catheter and the distal end of the balloon.

3. The balloon catheter according to claim 2 wherein the tubular member comprises a cylindrical cross-section having a central passageway through which the stiffening member extends, the central passageway having a diameter that is sufficiently greater than an outside diameter of the stiffening member so as to provide a gap therebetween.

4. The balloon catheter according to claim 3 wherein the tubular member further comprises a plurality of openings through a wall thereof, the plurality of openings being disposed circumferentially about and longitudinally along the tubular member.

5. The balloon catheter according to claim 4 wherein the openings are disposed is a spiral pattern about the tubular member.

6. The balloon catheter according to claim 2 wherein the tubular member comprises a star-shaped cross-section having an exterior surface defined by a plurality of alternating peaks and valleys, the peaks being configured to prevent the balloon, when deflated, from occluding the valleys.

7. The balloon catheter according to claim 1 wherein the deflation mechanism comprises a series of protrusions disposed about an exterior surface of the stiffening member, the protrusions being configured to prevent the balloon, when deflated, from engaging at least a portion of the exterior surface of the stiffening member adjacent to the protrusions.

8. The balloon catheter according to claim 1 wherein the deflation mechanism comprises a series of grooves disposed along an exterior surface of the stiffening member, the grooves being configured to prevent occlusion thereof by the balloon when in a deflated state.

9. The balloon catheter according to claim 1 wherein the balloon wall comprises one of a non-elastic material, a non-compliant material, and a semi-rigid material.

10. The balloon catheter according to claim 1 wherein the stiffening member comprises an elongate proximal portion extending longitudinally through the lumen of the shaft of the catheter, the proximal portion of the stiffening member having a cross-sectional area that is less than a cross-sectional area of the lumen to facilitate the flow of an inflation fluid through the lumen.

11. The balloon catheter according to claim 1 wherein the stiffening member comprises an elongate nitinol wire.

12. The balloon catheter according to claim 1 wherein the deflation mechanism comprises a tubular member disposed within the interior volume of the balloon and between the distal end portion of the catheter and the end cap, and further wherein proximal axial movement of the distal end of the balloon relative to the proximal end of the balloon in the direction generally parallel to the axis of the shaft is limited by the tubular member.

13. The balloon catheter according to claim 1 wherein the sleeve comprises a distal terminus that is spaced away from the distal end of the stiffening member so as to permit axial movement of the distal end of the balloon relative to the distal end of the stiffening member.

14. The balloon catheter according to claim 1 further comprising an inflation device for inflating or deflating said balloon, said inflation device being attached to the connector on the proximal end portion of the catheter.

15. A balloon catheter comprising:
- a inflatable balloon comprising a balloon wall defining an interior volume, the balloon further comprising a distal end, a proximal end, and a central portion disposed therebetween;
- a catheter comprising an elongated shaft extending along an axis between a distal end portion and a proximal end portion, the proximal end portion comprising a connector configured to engage an inflation device, the distal end portion fixedly connected to the proximal end of the balloon, the distal end portion comprising an aperture near the proximal end of the balloon, a lumen extending through the shaft and in fluid communication with the interior volume of the balloon via the aperture;
- a stiffening member extending distally from the distal end portion of the catheter and through the interior volume of the balloon, the stiffening member being engaged with the distal end of the balloon; and
- a deflation mechanism disposed at least partially about the stiffening member, the deflation mechanism configured to facilitate the flow of an inflation fluid through the interior volume of the balloon and towards the aperture,
- wherein the deflation mechanism comprises a tubular member disposed within the interior volume of the balloon and between the distal end portion of the catheter and the distal end of the balloon, the tubular member comprising a star-shaped cross-section having an exterior surface defined by a plurality of alternating peaks and valleys, the peaks being configured to prevent the balloon, when deflated, from occluding the valleys.

\* \* \* \* \*